US011437146B2

(12) United States Patent
Fukunishi

(10) Patent No.: US 11,437,146 B2
(45) Date of Patent: Sep. 6, 2022

(54) DISEASE DEVELOPMENT RISK PREDICTION SYSTEM, DISEASE DEVELOPMENT RISK PREDICTION METHOD, AND DISEASE DEVELOPMENT RISK PREDICTION PROGRAM

(71) Applicant: NEC CORPORATION, Tokyo (JP)

(72) Inventor: Hiroaki Fukunishi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 79 days.

(21) Appl. No.: 16/637,492

(22) PCT Filed: Aug. 9, 2017

(86) PCT No.: PCT/JP2017/028872
§ 371 (c)(1),
(2) Date: Feb. 7, 2020

(87) PCT Pub. No.: WO2019/030840
PCT Pub. Date: Feb. 14, 2019

(65) Prior Publication Data
US 2020/0251219 A1 Aug. 6, 2020

(51) Int. Cl.
*G16H 50/30* (2018.01)
*G16H 70/60* (2018.01)
(Continued)

(52) U.S. Cl.
CPC ............. *G16H 50/30* (2018.01); *G06Q 40/08* (2013.01); *G16H 50/20* (2018.01); *G16H 70/40* (2018.01);
(Continued)

(58) Field of Classification Search
CPC ..... G16H 50/20; G16H 50/30; G01N 2800/50
See application file for complete search history.

(56) References Cited

U.S. PATENT DOCUMENTS

| 2013/0262357 A1* | 10/2013 | Amarasingham ...... G16H 50/70 706/21 |
| 2014/0074509 A1* | 3/2014 | Amarasingham ...... G16H 50/70 705/3 |
| 2017/0029889 A1* | 2/2017 | Cargill .................... A61P 29/00 |

FOREIGN PATENT DOCUMENTS

| JP | 2008-083847 A | 4/2008 |
| JP | 4981305 B2 | 7/2012 |

(Continued)

OTHER PUBLICATIONS

International Search Report for PCT/JP2017/028872 dated Oct. 31, 2017 [PCT/ISA/210].
(Continued)

*Primary Examiner* — Reginald R Reyes

(57) ABSTRACT

A disease development risk prediction system 10 includes: a data generation means 11 which generates combination data by combining at least two different types of receipt data using a combination key, wherein the receipt data includes an insured person number for an insured person which was converted using a predetermined method, a birth date or birth year and month which are both age-identifiable items, and gender, and the combination key combines the converted insured person number, age-identifiable items, and gender; and a model generation means 12 which uses the generated combination data to generate a prediction model predicting a risk of the insured person of developing a predetermined disease.

15 Claims, 19 Drawing Sheets

(51) Int. Cl.
*G16H 50/20* (2018.01)
*G16H 70/40* (2018.01)
*G06Q 40/08* (2012.01)
*H04L 9/06* (2006.01)

(52) U.S. Cl.
CPC .......... *G16H 70/60* (2018.01); *H04L 9/0643* (2013.01); *H04L 2209/42* (2013.01)

(56) References Cited

FOREIGN PATENT DOCUMENTS

| | | |
|---|---|---|
| JP | 2014-052822 A | 3/2014 |
| JP | 5603639 B2 | 10/2014 |
| JP | 2015-090689 A | 5/2015 |
| JP | 2017-117469 A | 6/2017 |
| WO | 2015/071968 A1 | 5/2015 |

OTHER PUBLICATIONS

Written Opinion for PCT/JP2017/028872 dated Oct. 31, 2017 [PCT/ISA/237].

* cited by examiner

FIG. 3

| TYPE | MEDICAL RECEIPT |
|---|---|
| ITEM NUMBER | ITEM NAME |
| 1 | RECEPTION NUMBER |
| 2 | MEDICAL INSTITUTION CODE |
| 3 | RECEPTION COUNT |
| 4 | RECEIPT TYPE |
| 5 | MEDICAL CARE YEAR AND MONTH |
| 6 | PATIENT NAME |
| 7 | MALE/FEMALE |
| 8 | BIRTH DATE |
| 9 | INSURER NUMBER |
| 10 | INSURANCE CERTIFICATE NUMBER |
| 11 | ADMISSION YEAR, MONTH, AND DAY |
| 12 | INPATIENT/OUTPATIENT |
| ⋮ | ⋮ |

FIG. 5

| TYPE | DISPENSING RECEIPT |
|---|---|
| ITEM NUMBER | ITEM NAME |
| 1 | RECEPTION NUMBER |
| 2 | PHARMACY CODE |
| 3 | RECEPTION COUNT |
| 4 | RECEIPT NUMBER |
| 5 | DISPENSING YEAR AND MONTH |
| 6 | RECEIPT TYPE |
| 7 | INSURER NUMBER |
| 8 | INSURANCE CERTIFICATE NUMBER |
| 9 | NAME IN KANJI |
| 10 | MALE/FEMALE |
| 11 | BIRTH DATE |
| 12 | AGE |
| 13 | AGE IDENTIFICATION |
| 14 | BENEFIT PROPORTION |
| 15 | MEDICAL INSTITUTION CODE |
| 16 | TOTAL MEDICAL COST |
| ⋮ | ⋮ |

FIG. 6

INSURED PERSON NUMBER IS TYPICALLY PROVIDED IN HASHED FORM

MONTHLY DATA

| RECEIPT NUMBER | INSURANCE IDENTIFICATION NUMBER | INSURED PERSON NUMBER | GENDER | BIRTH DATE | SERVICE ITEM POINT | NURSING CARE CONDITION CLASS CODE (NURSING CARE LEVEL) | COPAYMENT | ... |
|---|---|---|---|---|---|---|---|---|
| 11111 | 12345678 | 1111111 | 1 | 40212 | 1000 | 1 | 2000 | ... |
| 22222 | 23456789 | 2222222 | 2 | 40314 | 2000 | 2 | 3000 | ... |
| 33333 | 34567891 | 3333333 | 1 | 40520 | 2500 | 3 | 500 | ... |
| 44444 | 45678912 | 4444444 | 1 | 41213 | 800 | 2 | 3500 | ... |
| 55555 | 56789123 | 5555555 | 2 | 40701 | 400 | 5 | 700 | ... |
| 66666 | 67891234 | 6666666 | 1 | 41109 | 1500 | 3 | 200 | ... |
| ... | ... | ... | ... | ... | ... | ... | ... | ... |

MONTHLY

FIG. 7

| TYPE | NURSING CARE INSURANCE DATA |
|---|---|
| ITEM NUMBER | ITEM NAME |
| 1 | INSURED PERSON NAME (KANA) |
| 2 | NURSING CARE INSURER NUMBER |
| 3 | INSURED PERSON NUMBER |
| 4 | BENEFIT RESULT DELIVERY TARGET YEAR AND MONTH |
| 5 | BIRTH DATE |
| 6 | GENDER CODE |
| 7 | QUALIFICATION ACQUISITION YEAR, MONTH, AND DAY |
| 8 | QUALIFICATION LOSS YEAR, MONTH, AND DAY |
| 9 | BENEFIT RESULT SPECIFICATION COUNT |
| 10 | BENEFIT RESULT SPECIFICATION PUBLIC EXPENSE COUNT |
| 11 | BENEFIT RESULT SPECIFICATION SERVICE POINT |
| 12 | BENEFIT RESULT SPECIFICATION PUBLIC EXPENSE SERVICE POINT |
| 13 | APPLICATION YEAR, MONTH, AND DAY |
| 14 | DEEMED NURSING CARE CLASS CODE |
| 15 | NURSING CARE CONDITION CLASS CODE |
| 16 | APPROVAL VALID PERIOD (START YEAR, MONTH, AND DAY) |
| 17 | APPROVAL VALID PERIOD (END YEAR, MONTH, AND DAY) |
| 18 | SERVICE ITEM POINT (AFTER DECISION) |
| ⋮ | ⋮ |

FIG. 8

| PERSONAL IDENTIFI-CATION | YEAR | GENDER | AGE | ANNUAL MEDICAL CARE COST | ANNUAL RECEIPT COUNT OF INJURY/DISEASE 1 | ANNUAL RECEIPT COUNT OF INJURY/DISEASE 2 | ... | ANNUAL DISPENSING COST | ANNUAL RECEIPT COUNT OF DRUG 1 | ANNUAL RECEIPT COUNT OF DRUG 2 | ... | NURSING CARE SERVICE ITEM POINT | NURSING CARE CONDITION CLASS CODE (NURSING CARE LEVEL) | COPAYMENT | ANNUAL USE COUNT OF NURSING CARE SERVICE 1 | ... |
|---|---|---|---|---|---|---|---|---|---|---|---|---|---|---|---|---|
| 1234 5678 | 2011 | 1 | 50 | 1000 | 1 | 8 | ... | 1000 | 1 | 8 | ... | 1000 | 1 | 2000 | 8 | ... |
| 2345 6789 | 2011 | 2 | 51 | 2000 | 2 | 3 | ... | 2000 | 2 | 3 | ... | 2000 | 2 | 3000 | 2 | ... |
| 3456 7891 | 2012 | 1 | 52 | 2500 | 12 | 10 | ... | 2500 | 12 | 10 | ... | 2500 | 3 | 500 | 3 | ... |
| 4567 8912 | 2012 | 1 | 53 | 800 | 5 | 0 | ... | 800 | 5 | 0 | ... | 800 | 2 | 3500 | 15 | ... |
| 5678 9123 | 2013 | 2 | 54 | 400 | 8 | 5 | ... | 400 | 8 | 5 | ... | 400 | 5 | 700 | 10 | ... |
| 6789 1234 | 2013 | 1 | 55 | 1500 | 2 | 2 | ... | 1500 | 2 | 2 | ... | 1500 | 3 | 200 | 4 | ... |
| ... | ... | ... | ... | ... | ... | ... | ... | ... | ... | ... | ... | ... | ... | ... | ... | ... |

FIG. 9

| ... | YEAR X-1 | YEAR X | YEAR X+1 | YEAR X+2 | YEAR X+3 | ... |
|---|---|---|---|---|---|---|
| ... | EXPLANATORY VARIABLE | EXPLANATORY VARIABLE | OBJECTIVE VARIABLE | OBJECTIVE VARIABLE | OBJECTIVE VARIABLE | ... |

FIG. 10

MEDICAL RECEIPTS OF Z × 12 MONTHS

| PERSONAL IDENTIFICATION | ... | YEAR X-1 | YEAR X | YEAR X+1 | YEAR X+2 | YEAR X+3 | ... |
|---|---|---|---|---|---|---|---|
| 12345678 | | ~ | ~ | | | | ... |
| 23456789 | | ~ | ~ | | | | |
| 34567891 | | ~ | ~ | | | | |
| 45678912 | | ~ | ~ | | | | |
| 56789123 | | ~ | ~ | | | | |
| 67891234 | | INJURY/ DISEASE Y | INJURY/ DISEASE Y | | | | | ⇦ REMOVE
| ... | ... | ... | ... | ... | ... | ... | ... |

FIG. 11

| PERSONAL IDENTIFICATION | ... | YEAR X-1 | YEAR X | YEAR X+1 | YEAR X+2 | YEAR X+3 | ... | OBJECTIVE VARIABLE |
|---|---|---|---|---|---|---|---|---|
| 12345678 | | 1 | 1 | INJURY/ DISEASE Y | | | ... | 1 |
| 23456789 | | 1 | 1 | | | | | 0 |
| 34567891 | | 1 | 1 | | | | | 0 |
| 45678912 | | 1 | 1 | | INJURY/ DISEASE Y | | | 1 |
| 56789123 | | 1 | 1 | | | | | 0 |
| ... | ... | ... | ... | ... | ... | ... | ... | ... |

FIG. 13

| AGE | GENDER | NURSING CARE LEVEL | NURSING CARE SERVICE USE | DISEASE 1 | DISEASE 2 | DISEASE 3 | DISEASE 4 | DISEASE 5 | DRUG EFFICACY 1 | DRUG EFFICACY 2 | DRUG EFFICACY 3 | DRUG EFFICACY 4 | DRUG EFFICACY 5 | OBJECTIVE VARIABLE |
|---|---|---|---|---|---|---|---|---|---|---|---|---|---|---|
| 75 | 1 | 1 | 1 | 1 | 1 | 1 | 1 | 1 | 1 | 1 | 1 | 1 | 1 | 0 |
| 76 | 0 | 2 | 0 | 0 | 0 | 0 | 0 | 0 | 0 | 0 | 0 | 0 | 0 | 0 |
| 77 | 1 | 3 | 1 | 1 | 1 | 1 | 0 | 1 | 1 | 1 | 1 | 1 | 1 | 1 |
| 78 | 0 | 4 | 0 | 0 | 0 | 0 | 0 | 0 | 0 | 0 | 0 | 0 | 0 | 0 |
| 79 | 1 | 5 | 1 | 0 | 1 | 0 | 0 | 0 | 0 | 1 | 0 | 1 | 0 | 0 |
| 80 | 0 | 6 | 1 | 1 | 1 | 1 | 1 | 1 | 1 | 1 | 1 | 1 | 1 | 1 |
| 81 | 1 | 7 | 1 | 0 | 1 | 0 | 1 | 0 | 0 | 1 | 0 | 1 | 0 | 0 |
| 82 | 0 | 1 | 1 | 1 | 1 | 1 | 1 | 1 | 1 | 1 | 1 | 1 | 1 | 1 |
| 83 | 1 | 2 | 1 | 1 | 1 | 0 | 1 | 1 | 1 | 1 | 1 | 1 | 1 | 1 |
| 84 | 1 | 5 | 1 | 1 | 0 | 0 | 0 | 1 | 0 | 1 | 0 | 0 | 1 | 0 |

FIG. 15

TRAINING DATA

| AGE | GENDER | NURSING CARE LEVEL | NURSING CARE SERVICE USE | DISEASE 1 | DISEASE 2 | DISEASE 3 | DISEASE 4 | DISEASE 5 | DRUG EFFICACY 1 | DRUG EFFICACY 2 | DRUG EFFICACY 3 | DRUG EFFICACY 4 | DRUG EFFICACY 5 | OBJECTIVE VARIABLE |
|---|---|---|---|---|---|---|---|---|---|---|---|---|---|---|
| 75 | 1 | 1 | 1 | 1 | 1 | 1 | 1 | 1 | 1 | 1 | 1 | 1 | 1 | 0 |
| 76 | 0 | 2 | 0 | 0 | 0 | 0 | 0 | 0 | 0 | 0 | 0 | 0 | 0 | 0 |
| 77 | 1 | 3 | 1 | 1 | 1 | 1 | 0 | 1 | 1 | 0 | 1 | 1 | 1 | 1 |
| 78 | 0 | 4 | 0 | 0 | 0 | 0 | 0 | 0 | 0 | 0 | 0 | 0 | 0 | 0 |
| 79 | 1 | 5 | 1 | 0 | 1 | 1 | 1 | 1 | 0 | 1 | 0 | 1 | 0 | 0 |
| 80 | 0 | 6 | 1 | 1 | 1 | 1 | 1 | 1 | 1 | 1 | 1 | 1 | 1 | 1 |
| 81 | 1 | 7 | 1 | 0 | 1 | 0 | 1 | 0 | 0 | 1 | 0 | 1 | 0 | 0 |

EVALUATION DATA

| AGE | GENDER | NURSING CARE LEVEL | NURSING CARE SERVICE USE | DISEASE 1 | DISEASE 2 | DISEASE 3 | DISEASE 4 | DISEASE 5 | DRUG EFFICACY 1 | DRUG EFFICACY 2 | DRUG EFFICACY 3 | DRUG EFFICACY 4 | DRUG EFFICACY 5 | OBJECTIVE VARIABLE |
|---|---|---|---|---|---|---|---|---|---|---|---|---|---|---|
| 82 | 0 | 1 | 1 | 1 | 1 | 1 | 1 | 1 | 1 | 1 | 1 | 1 | 1 | 1 |
| 83 | 1 | 2 | 1 | 1 | 1 | 1 | 1 | 1 | 1 | 1 | 1 | 1 | 1 | 1 |
| 84 | 1 | 5 | 1 | 1 | 0 | 1 | 0 | 1 | 0 | 1 | 0 | 0 | 1 | 0 |

FIG. 16

| AGE | GENDER | NURSING CARE LEVEL | NURSING CARE SERVICE USE | DISEASE 1 | DISEASE 2 | DISEASE 3 | DISEASE 4 | DISEASE 5 | DRUG EFFICACY 1 | DRUG EFFICACY 2 | DRUG EFFICACY 3 | DRUG EFFICACY 4 | DRUG EFFICACY 5 | OBJECTIVE VARIABLE |
|---|---|---|---|---|---|---|---|---|---|---|---|---|---|---|
| 78 | 0 | 4 | 0 | 0 | 0 | 0 | 0 | 0 | 0 | 0 | 0 | 0 | 0 | 0 |
| 79 | 1 | 5 | 1 | 0 | 1 | 0 | 1 | 0 | 0 | 1 | 0 | 1 | 0 | 0 |
| 80 | 0 | 6 | 1 | 1 | 1 | 1 | 1 | 1 | 1 | 1 | 1 | 1 | 1 | 1 |
| 81 | 1 | 7 | 1 | 0 | 1 | 0 | 1 | 0 | 0 | 1 | 0 | 1 | 0 | 0 |
| 82 | 0 | 1 | 1 | 1 | 1 | 1 | 1 | 1 | 1 | 1 | 1 | 1 | 1 | 0 |
| 83 | 1 | 2 | 1 | 1 | 1 | 1 | 1 | 1 | 1 | 1 | 1 | 1 | 1 | 1 |

ADJUST SO THAT OBJECTIVE VARIABLE IS 1:1

| AGE | GENDER | NURSING CARE LEVEL | NURSING CARE SERVICE USE | DISEASE 1 | DISEASE 2 | DISEASE 3 | DISEASE 4 | DISEASE 5 | DRUG EFFICACY 1 | DRUG EFFICACY 2 | DRUG EFFICACY 3 | DRUG EFFICACY 4 | DRUG EFFICACY 5 | OBJECTIVE VARIABLE |
|---|---|---|---|---|---|---|---|---|---|---|---|---|---|---|
| 79 | 1 | 5 | 1 | 0 | 1 | 0 | 1 | 0 | 0 | 1 | 0 | 1 | 0 | 0 |
| 80 | 0 | 6 | 1 | 1 | 1 | 1 | 1 | 1 | 1 | 1 | 1 | 1 | 1 | 1 |
| 81 | 1 | 7 | 1 | 0 | 1 | 0 | 1 | 0 | 0 | 1 | 0 | 1 | 0 | 0 |
| 83 | 1 | 2 | 1 | 1 | 1 | 1 | 1 | 1 | 1 | 1 | 1 | 1 | 1 | 1 |

FIG. 18

|  |  | PREDICTED CLASS | |
|---|---|---|---|
|  |  | Positive | Negative |
| ACTUAL CLASS | Positive | True Positive(TP) | False Negative(FN) |
| | Negative | False Positive(FP) | True Negative(TN) |

Accuracy = (TP+TN) / (TP+FP+TN+FN)
True Positive Rate = TP / (TP+FN)
False Negative Rate = FN / (TP+FN)
False Positive Rate = FP / (FP+TN)
True Negative Rate = TN / (FP+TN)
Precision = TP / (TP+FP)

DISEASE DEVELOPMENT RISK PREDICTION SYSTEM, DISEASE DEVELOPMENT RISK PREDICTION METHOD, AND DISEASE DEVELOPMENT RISK PREDICTION PROGRAM

CROSS REFERENCE TO RELATED APPLICATIONS

This application is a National Stage of International Application No. PCT/JP2017/028872 filed Aug. 9, 2017.

TECHNICAL FIELD

The present invention relates to a disease development risk prediction system, a disease development risk prediction method, and a disease development risk prediction program, and particularly relates to a disease development risk prediction system, a disease development risk prediction method, and a disease development risk prediction program for predicting the risk of insured persons developing a predetermined disease in the future.

BACKGROUND ART

In the national health insurance program operated by local governments and the health insurance program operated by health insurance societies established by corporations, the formulation of measures for reducing medical care costs on insured persons using the programs is promoted. When formulating such measures, for example, the health conditions of insured persons are analyzed using health care data such as receipts.

Health conditions are analyzed, for example, by artificial intelligence (AI). If future deterioration in the health conditions of insured persons is predicted, local governments or health insurance societies can plan to take measures such as activities to prevent deterioration in the health conditions of insured persons.

One cause of deterioration in health conditions is population aging. An increasing number of patients due to population aging is regarded as a major social problem currently in Japan. One reason why an increasing number of patients is regarded as a major social problem is that patient care requires enormous costs.

Costs for patient care include medical care cost, nursing care cost, and informal care cost, and the like. That is, with an increase in the number of patients, social costs borne by the national and local governments.

Informal care means not support provided on the basis of formal programs by local governments, specialized agencies, etc., but unofficial support provided by families, friends, local residents, volunteers, and the like and not on the basis of formal programs. Informal care is also referred to as informal service.

If the risk of insured persons developing a predetermined disease in the future can be predicted early, each local government or each health insurance society may be able to suppress the development of the predetermined disease by taking preventive measures. As a result of suppressing the development of the predetermined disease by insured persons, the foregoing social costs can be reduced.

Patent Literature (PTL) 1 and PTL 2 describe techniques of predicting, for example, the risk of developing a predetermined disease. For example, PTL 1 describes a method of predicting the risk of developing Alzheimer's disease.

The method described in PTL 1 predicts the risk of developing Alzheimer's disease by determining human lipocalin type prostaglandin D synthetase ($\beta$-trace) losing chaperone activity of amyloid $\beta$ peptide existing in biological fluid collected from a human. Alternatively, the method described in PTL 1 predicts the risk of developing Alzheimer's disease by measuring chaperone activity of amyloid $\beta$ peptide in a biological fluid collected from a human.

PTL 2 describes a method of, for example in treatment of primary breast cancer, predicting axillary lymph node (AxLN) metastasis (AxLN metastasis) using a prediction model formed by an alternative decision tree (AD tree). For example, a learning device for learning the prediction model described in PTL 2 uses clinical data obtained backward by tracing back to the past, as training data.

PTL 3 describes a medical data analysis system for predicting medical care cost reduction effect by health guidance, by generating and visualizing, on the basis of medical check-up information and receipt information, a graphical model having each item of the medical check-up information and the receipt information as a random variable.

CITATION LIST

Patent Literatures

PTL 1: Japanese Patent No. 4981305
PTL 2: Japanese Patent No. 5603639
PTL 3: Japanese Patent Application Laid-Open No. 2015-090689

SUMMARY OF INVENTION

Technical Problem

When performing the method described in PTL 1, special testing is required in order to predict the risk of developing Alzheimer's disease, as mentioned above. That is, the method described in PTL 1 does not assume predicting the risk of developing Alzheimer's disease using existing information which is available without special testing.

The learning device described in PTL 2 uses, as training data, clinical data which is existing information, as mentioned above. However, the learning device described in PTL 2 does not assume using data other than clinical data as training data.

The medical data analysis system described in PTL 3 generates and visualizes a graphical model by combining a plurality of sets of data from different sources, as mentioned above. However, the medical data analysis system described in PTL 3 does not assume concealing information for identifying individual persons when combining a plurality of sets of data.

Object of Invention

The present invention therefore has an object of providing a disease development risk prediction system, a disease development risk prediction method, and a disease development risk prediction program that can predict disease development risk on the basis of a plurality of sets of data from different sources while protecting personal information, to solve the problems stated above.

Solution to Problem

A disease development risk prediction system according to the present invention includes: a data generation means which generates combination data by combining at least two different types of receipt data using a combination key, wherein the receipt data includes an insured person number for an insured person which was converted using a predetermined method, a birth date or birth year and month which are both age-identifiable items, and gender, and the combination key combines the converted insured person number, age-identifiable items, and gender; and a model generation means which uses the generated combination data to generate a prediction model predicting a risk of the insured person of developing a predetermined disease.

A disease development risk prediction method according to the present invention includes: generating combination data by combining at least two different types of receipt data using a combination key, wherein the receipt data includes an insured person number for an insured person which was converted using a predetermined method, a birth date or birth year and month which are both age-identifiable items, and gender, and the combination key combines the converted insured person number, age-identifiable items, and gender; and using the generated combination data to generate a prediction model predicting a risk of the insured person of developing a predetermined disease.

A disease development risk prediction program according to the present invention causes a computer to execute: a first generation process of generating combination data by combining at least two different types of receipt data using a combination key, wherein the receipt data includes an insured person number for an insured person which was converted using a predetermined method, a birth date or birth year and month which are both age-identifiable items, and gender, and the combination key combines the converted insured person number, age-identifiable items, and gender; and a second generation process of using the generated combination data to generate a prediction model predicting a risk of the insured person of developing a predetermined disease.

Advantageous Effects of Invention

According to the present invention, disease development risk can be predicted on the basis of a plurality of sets of data from different sources while protecting personal information.

BRIEF DESCRIPTION OF DRAWINGS

FIG. 3 is an explanatory diagram showing an example of items included in a medical receipt.

FIG. 5 is an explanatory diagram showing an example of items included in a dispensing receipt.

FIG. 6 is an explanatory diagram showing an example of nursing care insurance data stored in a nursing care insurance data storage means 113.

FIG. 7 is an explanatory diagram showing an example of items included in nursing care insurance data.

FIG. 8 is an explanatory diagram showing an example of processed data aggregated in a personal unit, which is generated by a generation data processing means 121.

FIG. 9 is an explanatory diagram showing an example of use of processed data.

FIG. 10 is an explanatory diagram showing an example of a process for processed data by a data classification means 123.

FIG. 11 is an explanatory diagram showing another example of a process for processed data by the data classification means 123.

FIG. 13 is an explanatory diagram showing an example of data aggregated in a personal unit, which is generated by the data classification means 123.

FIG. 15 is an explanatory diagram showing an example of training data and evaluation data.

FIG. 16 is an explanatory diagram showing an example of a process for training data by the data classification means 123.

FIG. 18 is an explanatory diagram showing an example of values representing performance computed on the basis of a mixing matrix.

DESCRIPTION OF EXEMPLARY EMBODIMENT

Exemplary Embodiment 1

Description of Structure

Figure 1:
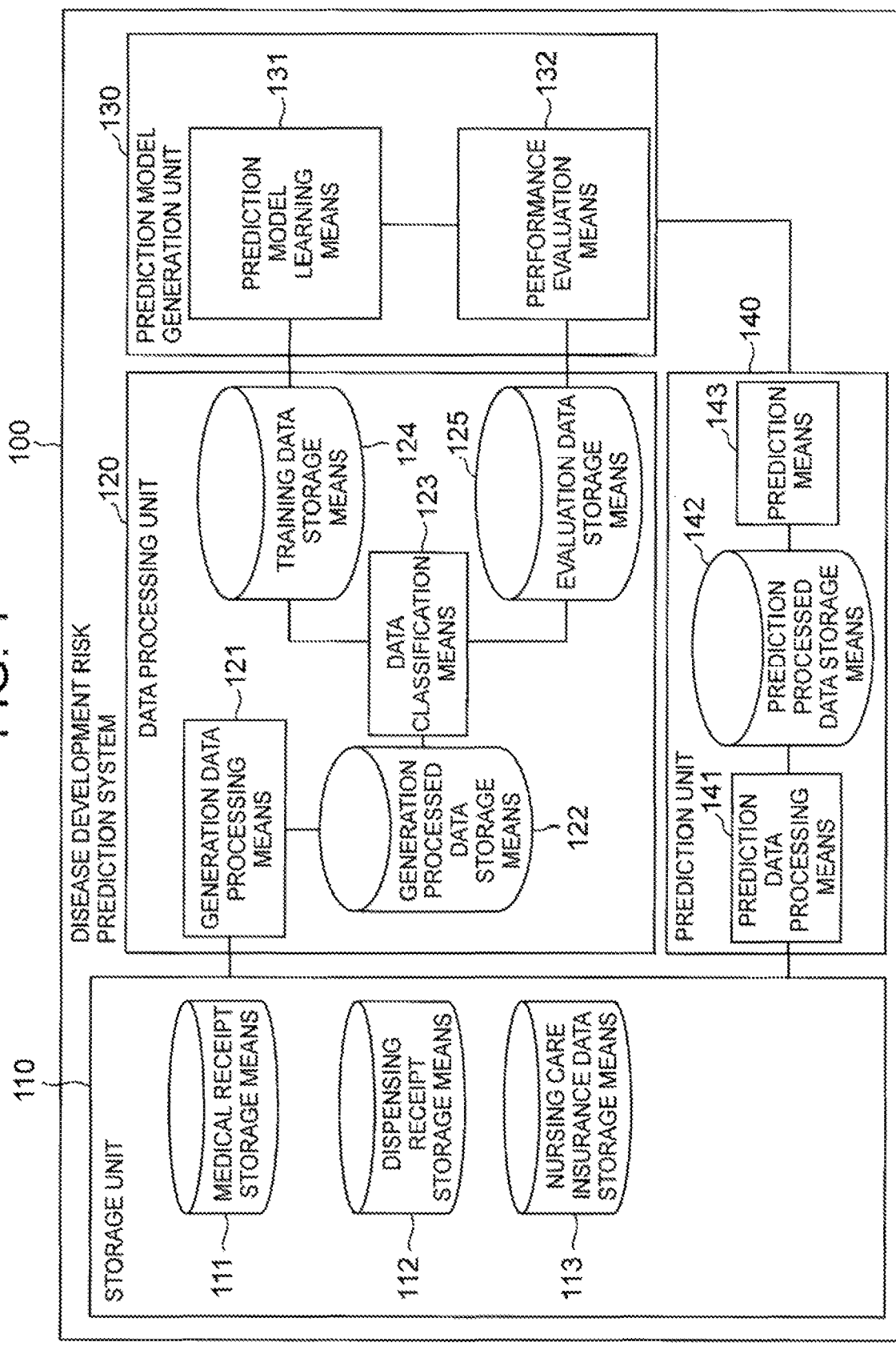
FIG. 1 is a block diagram showing an example of a structure of Exemplary embodiment 1 of a disease development risk prediction system according to the present invention.

An exemplary embodiment of the present invention will be described below, with reference to the drawings. FIG. 1 is a block diagram showing an example of a structure of Exemplary embodiment 1 of a disease development risk prediction system according to the present invention. The disease development risk prediction system according to this exemplary embodiment is a system for predicting the risk of insured persons developing a predetermined disease in the future.

A disease development risk prediction system 100 according to this exemplary embodiment uses, for generation of a prediction model for predicting disease development risk, data obtained by aggregating various data such as medical receipts and dispensing receipts in a personal unit, as training data for prediction model generation.

The disease development risk prediction system 100 according to this exemplary embodiment includes a storage unit 110, a data processing unit 120, a prediction model generation unit 130, and a prediction unit 140, as shown in FIG. 1.

The storage unit 110 includes a medical receipt storage means 111, a dispensing receipt storage means 112, and a nursing care insurance data storage means 113, as shown in FIG. 1. Data stored in each storage means may be raw data which is data not subjected to editing and the like, or data obtained as a result of a data provider processing raw data.

Figure 2:
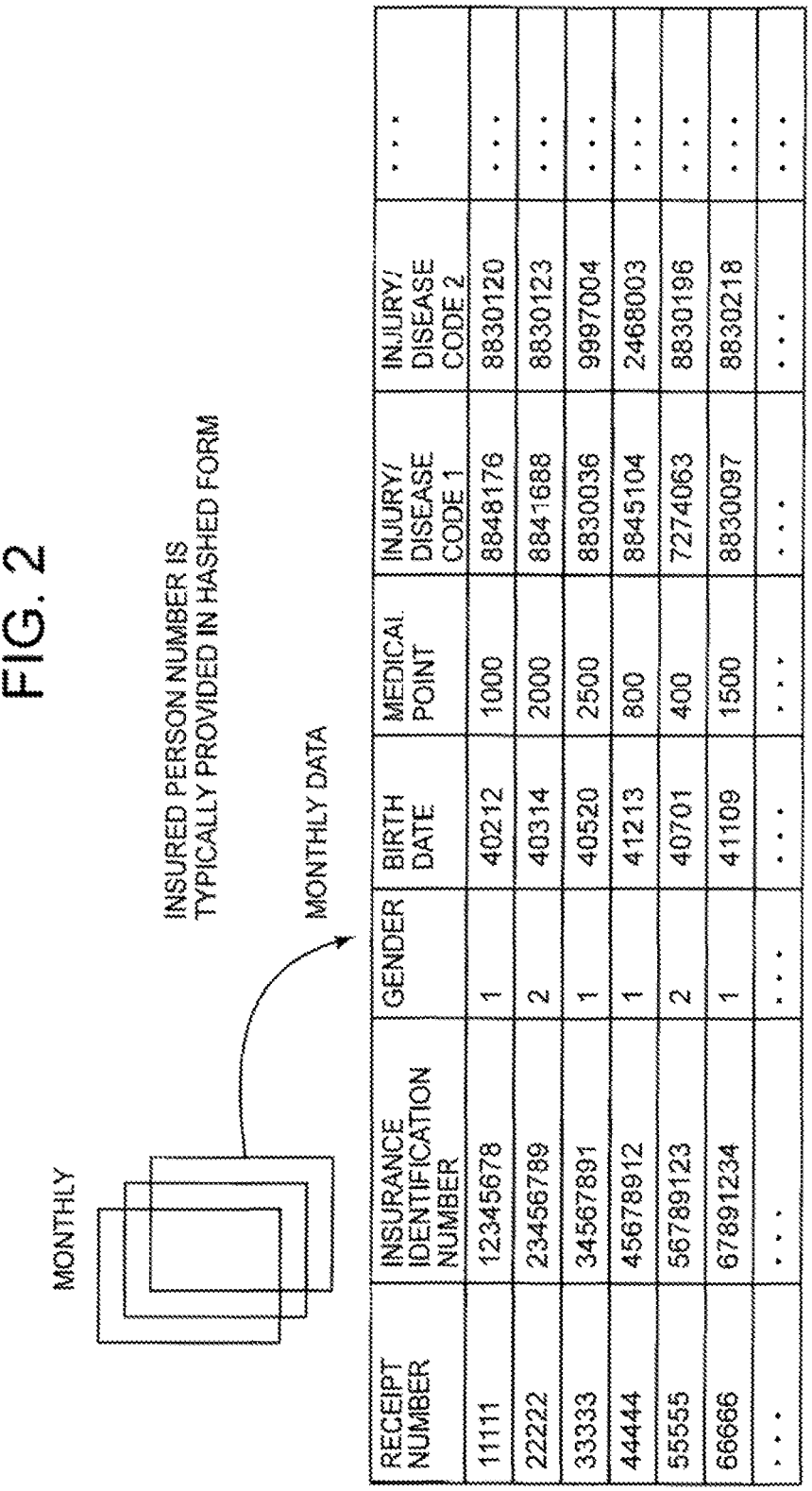
FIG. 2 is an explanatory diagram showing an example of medical receipts stored in a medical receipt storage means 111.

FIG. 2 is an explanatory diagram showing an example of medical receipts stored in the medical receipt storage means 111. A medical receipt is, for example, a statement indicating expenses paid for a medical act (or medical acts) at a hospital. A medical receipt is data provided by each medical institution.

As shown in FIG. 2, for example, each medical receipt includes receipt number, insurance identification number, gender, birth date, medical point, and injury/disease code. The receipt number is a number for uniquely identifying the medical receipt.

The insurance identification number is a number in the national health insurance program for uniquely identifying a household of an insured person who has received the medical act corresponding to the receipt number. The gender indicates a number representing the gender of the insured person who has received the medical act corresponding to the receipt number. The birth date indicates a number representing the birth date of the insured person who has received the medical act corresponding to the receipt number.

The medical point indicates a number representing expenses paid for the medical act corresponding to the receipt number. The injury/disease code is a number for uniquely identifying an injury/disease subjected to the medical act corresponding to the receipt number.

Each medical receipt is provided as monthly data, as shown in FIG. 2. When providing the medical receipt, the insurance identification number is normally hashed for personal information protection.

Each medical receipt may include items other than the items shown in FIG. 2. FIG. 3 is an explanatory diagram showing an example of items included in a medical receipt.

Figure 4:
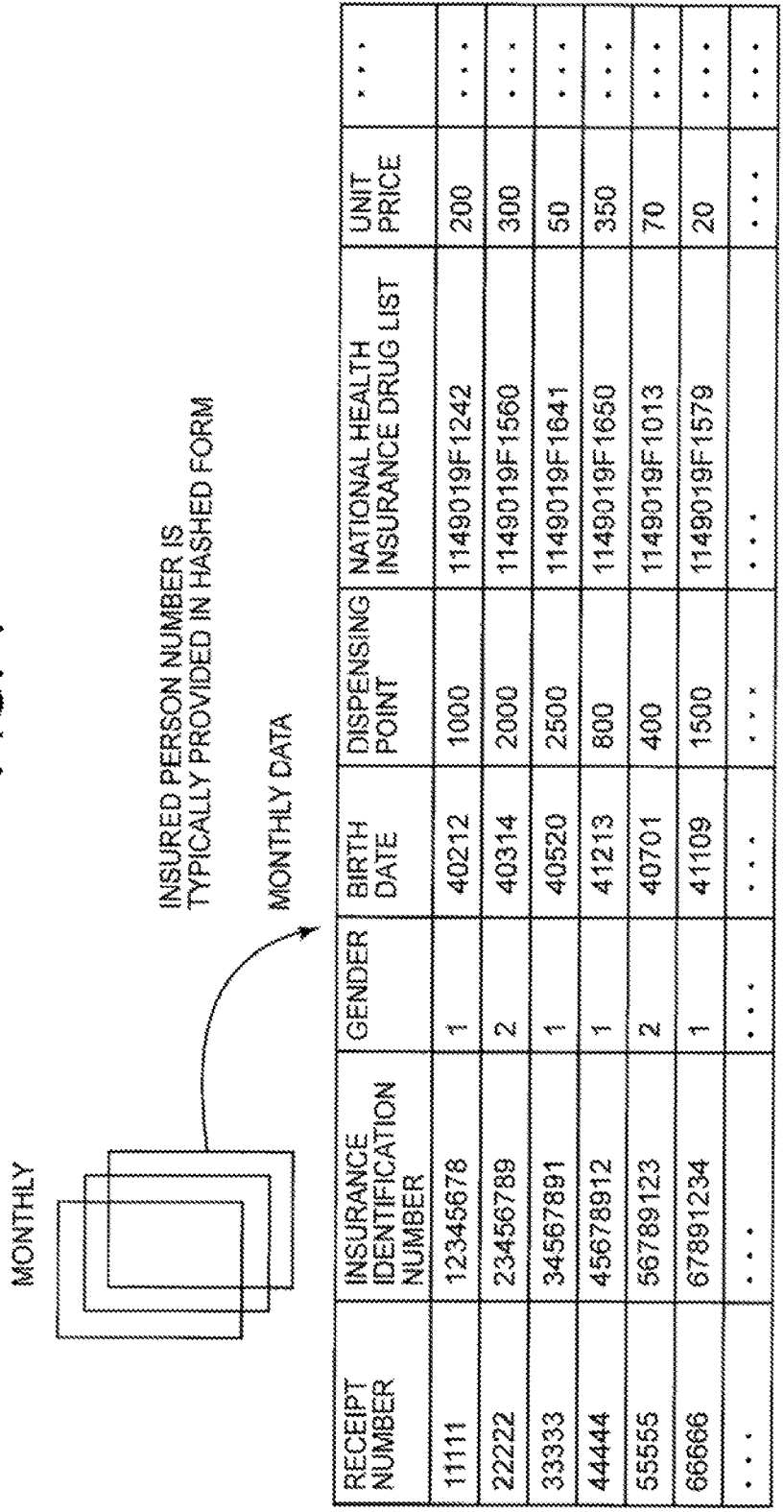
FIG. 4 is an explanatory diagram showing an example of dispensing receipts stored in a dispensing receipt storage means 112.

FIG. 4 is an explanatory diagram showing an example of dispensing receipts stored in the dispensing receipt storage means 112. A dispensing receipt is, for example, a statement indicating expenses paid for a dispensing act (or dispensing acts) at a dispensing pharmacy. A dispensing receipt is data provided by each dispensing pharmacy.

As shown in FIG. 4, for example, each dispensing receipt includes receipt number, insurance identification number, gender, birth date, dispensing point, national health insurance drug list, and unit price.

The receipt number is a number for uniquely identifying the dispensing receipt. The insurance identification number, the gender, and the birth date represent the same information as the respective items in the medical receipt.

The dispensing point indicates a number representing expenses paid for the dispensing act corresponding to the receipt number. The national health insurance drug list is a number for uniquely identifying a drug prescribed in the dispensing act corresponding to the receipt number. The unit price indicates the price of the drug represented by the national health insurance drug list.

Each dispensing receipt is provided as monthly data, as shown in FIG. 4. When providing the dispensing receipt, the insurance identification number is normally hashed for protection of personal information.

Each dispensing receipt may include items other than the items shown in FIG. 4. FIG. 5 is an explanatory diagram showing an example of items included in a dispensing receipt.

FIG. 6 is an explanatory diagram showing an example of nursing care insurance data stored in the nursing care insurance data storage means 113. Nursing care insurance data is, for example, a statement indicating expenses paid for a nursing care service at a nursing care facility. Nursing care insurance data is data provided by each nursing care facility.

As shown in FIG. 6, for example, nursing care insurance data includes receipt number, insurance identification number, insured person number, gender, birth date, service item point, nursing care condition class code (nursing care level), and copayment.

The receipt number is a number for uniquely identifying the nursing care insurance data. The insurance identification number, the gender, and the birth date represent the same information as the respective items in the medical receipt.

That is, when the insurance identification number is used, the nursing care insurance data and the medical receipt and the dispensing receipt of the same household are combined. The insured person number is a number in the nursing care insurance program for uniquely identifying an insured person who has received the nursing care service corresponding to the receipt number.

The service item point indicates a number representing expenses paid for the nursing care service corresponding to the receipt number. The nursing care condition class code (nursing care level) is a number representing the level of nursing care needed for the insured person indicated by the insured person number. The nursing care condition class code takes any number of 1 to 7. The copayment is the insured person's share of the expenses paid for the nursing care service corresponding to the receipt number.

Nursing care insurance data is provided as monthly data, as shown in FIG. 6. When providing the nursing care insurance data, the insurance identification number and the insured person number are normally hashed for protection of personal information.

Nursing care insurance data may include items other than the items shown in FIG. 6. FIG. 7 is an explanatory diagram showing an example of items included in nursing care insurance data.

The respective formats of medical receipts, dispensing receipts, and nursing care insurance data each depend on the system of the source of data, the processing of data in the source, and the like, and accordingly are not limited to the examples shown in FIGS. 2, 4, and 6.

In the case where insurance identification numbers in these types of data in this exemplary embodiment are the same number, they are hashed into the same value. The storage unit 110 may include a storage means for storing a registry indicating a list of insurance identification numbers, and/or a storage means for storing a registry indicating a list of insured person numbers.

The data processing unit 120 has a function of acquiring data relating to a predetermined disease for each insured person from medical receipts, dispensing receipts, and nursing care insurance data, to generate a prediction model for the risk of developing the predetermined disease.

The data processing unit 120 includes a generation data processing means 121, a generation processed data storage means 122, a data classification means 123, a training data storage means 124, and an evaluation data storage means 125, as shown in FIG. 1.

The generation data processing means 121 has a function of generating processed data which is data obtained by aggregating various data input from the storage unit 110 in a personal unit. An example of a method whereby the generation data processing means 121 generates processed data aggregated in a personal unit will be described below.

A personal code for uniquely identifying an individual person is basically deleted from raw data for personal information protection. Hence, to aggregate various data in a personal unit, the generation data processing means 121 uses data combining insurance identification number, gender, and age, as a combination key.

That is, when generating processed data, the generation data processing means 121 combines various data input using, for example, data combining hashed insurance identification number, gender, and age as a combination key. With the foregoing method, approximately uniquely identifiable processed data of each insured person is generated while protecting personal information.

Specifically, the generation data processing means 121 can generate processed data distinguishable for each insured person, except twins of the same sex in the same household. In the case where a personal code such as a national identification number is provided, the generation data processing means 121 may aggregate various data in a personal unit by directly using the personal code.

FIG. 8 is an explanatory diagram showing an example of processed data aggregated in a personal unit, which is generated by the generation data processing means 121. The processed data shown in FIG. 8 includes personal identification, year, gender, age, annual medical care cost, annual receipt count of each injury/disease, annual dispensing cost, annual receipt count of each drug, nursing care service item point, nursing care condition class code (nursing care level), copayment, and annual use count of each nursing care service.

The personal identification indicates a number representing the foregoing combination data. The year indicates the year subjected to data aggregation. The generation data processing means 121 in this exemplary embodiment generates processed data on a yearly basis. The gender represents the same information as the gender in the medical receipts, etc.

The age is the age of the insured person indicated by the personal identification, which is computed on the basis of fiscal years. For example, the age is computed from birth date. The age may be computed on the basis of years.

The annual medical care cost and the annual receipt count of each injury/disease are respectively obtained by computing the medical care cost sum and the total medical receipt count of each injury/disease in the target year on the basis of medical receipts. The annual receipt count of each injury/disease indicates the number of times the insured person received medical care for the injury/disease at medical institution in one year.

The annual receipt count of each injury/disease may be computed in terms of ICD-10 code which is an international unit, instead of in terms of injury/disease code. ICD-10 code is divided into code of large classification, code of middle classification, and code of small classification. The code of small classification is the minimum unit.

For example, the code of injury/disease name "diabetic nephropathy" is, when expressed as ICD-10 code, code of small classification "E142 (diabetic nephropathy)", code of middle classification "E14 (diabetes)", and code of large classification "E00-E90 (endocrine, nutritional and metabolic disease)".

Any of code of small classification, code of middle classification, code of large classification is used as an explanatory variable of the prediction model. However, in the case where code of small classification is used as an explanatory variable, the number of types of explanatory variables increases. In the case where code of large classification is used as an explanatory variable, the disease is generalized excessively.

Hence, code of middle classification is the most appropriate code as an explanatory variable. In the below-described examples, code of middle classification is used as an explanatory variable.

The annual dispensing cost and the annual receipt count of each drug are respectively obtained by computing the dispensing cost sum and the total dispensing receipt count of each drug in the target year on the basis of dispensing receipts. The annual receipt count of each drug indicates the number of times the insured person was prescribed the target drug at dispensing pharmacy in one year.

The national health insurance drug list representing the prescribed drug written in each dispensing receipt is the minimum unit. That is, in the case where the national health insurance drug list itself is used as an explanatory variable, the number of types of explanatory variables increases to 50,000 to 100,000.

In view of this, code representing drug efficacy as a result of generalizing the national health insurance drug list may be used as an explanatory variable. The number of types of codes representing drug efficacy are about several hundreds. For example, the national health insurance drug list of aspirin is "1143001X1015". The first to third digits of the national health insurance drug list are code representing drug efficacy. That is, the code representing drug efficacy of aspirin is "114 (antipyretic analgesics)".

The nursing care service item point, the copayment, and the annual use count of each nursing care service are respectively obtained by computing the nursing care service item point sum, the copayment sum, and the total nursing care insurance data count of each nursing care service in the target year on the basis of nursing care insurance data. The nursing care condition class code (nursing care level) is the nursing care condition class code of the insured person indicated by the personal identification, and therefore can be obtained directly from nursing care insurance data.

The processed data shown in FIG. 8 may include data representing the birth date of the insured person. However, given the possibility that the individual person is identified from the birth date, data representing the birth date is preferably not included for personal information protection.

For example, the processed data shown in FIG. 8 may include data representing the birth year and month of the insured person obtained by deleting the day from the data representing the birth date of the insured person. The generation data processing means 121 can generate processed data distinguishable for each insured person except twins of the same sex in the same household, even by using birth year and month.

The generation processed data storage means 122 has a function of storing the processed data aggregated in a personal unit, which is generated by the generation data processing means 121.

The data classification means 123 has a function of classifying the processed data stored in the generation processed data storage means 122 into data used for the generation of the prediction model (hereafter referred to as training data) and data used for the evaluation of the prediction model (hereafter referred to as evaluation data). The training data is stored in the training data storage means 124. The evaluation data is stored in the evaluation data storage means 125.

A method whereby the data classification means 123 generates training data and evaluation data used for the generation of the prediction model for the risk of developing the predetermined disease will be described below. In the case where processed data is generated on the basis of medical receipts, dispensing receipts, and nursing care insurance data of several years, the data classification means 123 designates each of the number of years of processed data used for generation of an explanatory variable and the number of years of processed data used for generation of an objective variable.

The data classification means 123 extracts only processed data of each insured person who did not developed the predetermined disease in the past including data of year X. That is, the data classification means 123 extracts processed data of each insured person for which the annual receipt count of injury/disease Y corresponding to the predetermined disease is all 0 throughout the designated number of years from among processed data aggregated in a personal unit.

Next, the data classification means 123 generates a flag that is an attribute indicating whether the insured person developed the predetermined disease from year (X+1) onward, as the objective variable. Flag "1" indicates that the insured person developed the predetermined disease. Flag "0" indicates that the insured person did not develop the predetermined disease.

The data classification means 123 determines whether the predetermined disease was developed, on the basis of the annual receipt count of injury/disease Yin the designated number of years in the processed data aggregated in a personal unit. Hereafter, processed data including an objective variable of flag "1" is referred to as a positive instance, and processed data including an objective variable of flag "0" is referred to as a negative instance.

FIG. 9 is an explanatory diagram showing an example of use of processed data. One row in FIG. 9 corresponds to one set of processed data. In this exemplary embodiment, processed data from year X backward is used as the explanatory variable of the model for predicting the risk of developing the predetermined disease, and the flag of processed data from year (X+1) onward is used as the objective variable of the model, as mentioned above.

FIG. 10 is an explanatory diagram showing an example of a process for processed data by the data classification means 123. One row in FIG. 10 corresponds to one set of processed data. The prediction model in this exemplary embodiment predicts the risk at which each insured person who has not developed the predetermined disease at the time of prediction develops the predetermined disease for the first time in the future.

Accordingly, the data classification means 123 deletes processed data from year X backward in which the annual receipt count of injury/disease Y corresponding to the predetermined disease is 1 or more (processed data in which the annual receipt count of injury/disease Y is 1 or more in the double line box in FIG. 10) from the samples, as shown in FIG. 10. That is, the data classification means 123 extracts only processed data of each insured person who did not develop the predetermined disease before or in year X.

The data classification means 123 may extract processed data for the explanatory variable relating to the predetermined disease in the following manner. In this example, consider the case of extracting processed data for the explanatory variable from processed data of Z years among processed data from year X backward. Processed data of Z years corresponds to a set of medical receipts of Z×12 months.

When the number of times the injury/disease code representing injury/disease Y appears in the set of medical receipts is larger, the certainty at which the insured person was affected with injury/disease Y is higher. In the case where the number of times the injury/disease code representing injury/disease Y appears is small, however, there is a possibility that injury/disease was not clear and the doctor diagnosed the insured person as being affected with injury/disease Y for the sake of convenience.

Hence, in the case where the number of times the injury/disease code representing injury/disease Y appears in the set of medical receipts is less than threshold k, the data classification means 123 in this exemplary embodiment may remove the corresponding processed data from the processed data for the explanatory variable, in order to more reliably determine whether the insured person was affected with injury/disease Y in the past. The threshold k is a value that may be changed freely. The foregoing determination method is particularly effective with regard to diseases that are difficult to diagnose.

FIG. 11 is an explanatory diagram showing another example of a process for processed data by the data classification means 123. One row in FIG. 11 corresponds to one set of processed data. In the case where, for processed data of each insured person who did not develop the predetermined disease before or in year X, the annual receipt count of injury/disease Y corresponding to the predetermined disease from year (X+1) onward (the annual receipt count of injury/disease Yin the double line box of the processed data shown in FIG. 11) is more than or equal to threshold k, the data classification means 123 sets flag "1" as the objective variable.

For example, when the disease has a low development rate, the number of years for which the annual receipt count of the injury/disease is checked for positive instance acquisition is large. By setting the flag, the data classification means 123 generates the objective variable used for learning the model for predicting the risk of developing the predetermined disease.

The data classification means 123 classifies the processed data generated by the foregoing method into training data and evaluation data in a predetermined proportion.

The prediction model generation unit 130 has a function of generating the model used to discriminate each insured person who has a potential to become a patient of the predetermined disease in the future using AI, machine learning, or the like. The prediction model generation unit 130 includes a prediction model learning means 131 and a performance evaluation means 132, as shown in FIG. 1.

The prediction model learning means 131 has a function of learning the prediction model using the training data stored in the training data storage means 124. The prediction model learning means 131 learns any model such as logistic regression or SVM (Support Vector Machine).

The performance evaluation means 132 has a function of evaluating the performance of predicting the risk of developing the predetermined disease by the generated prediction model using the evaluation data stored in the evaluation data storage means 125.

The prediction unit 140 has a function of predicting each insured person who has a potential to become a patient of the predetermined disease in the future, on the basis of new data. The prediction unit 140 includes a prediction data processing means 141, a prediction processed data storage means 142, and a prediction means 143, as shown in FIG. 1.

The prediction data processing means 141 has the same function as the generation data processing means 121. That is, the prediction data processing means 141 generates the processed data as shown in FIG. 8. The prediction processed data storage means 142 has a function of storing the processed data generated by the prediction data processing means 141.

The prediction means 143 has a function of predicting each insured person who has a potential to become a patient of the predetermined disease on the basis of the processed data stored in the prediction processed data storage means 142, using the prediction model learned by the prediction model learning means 131.

Description of Operation

Figure 12:
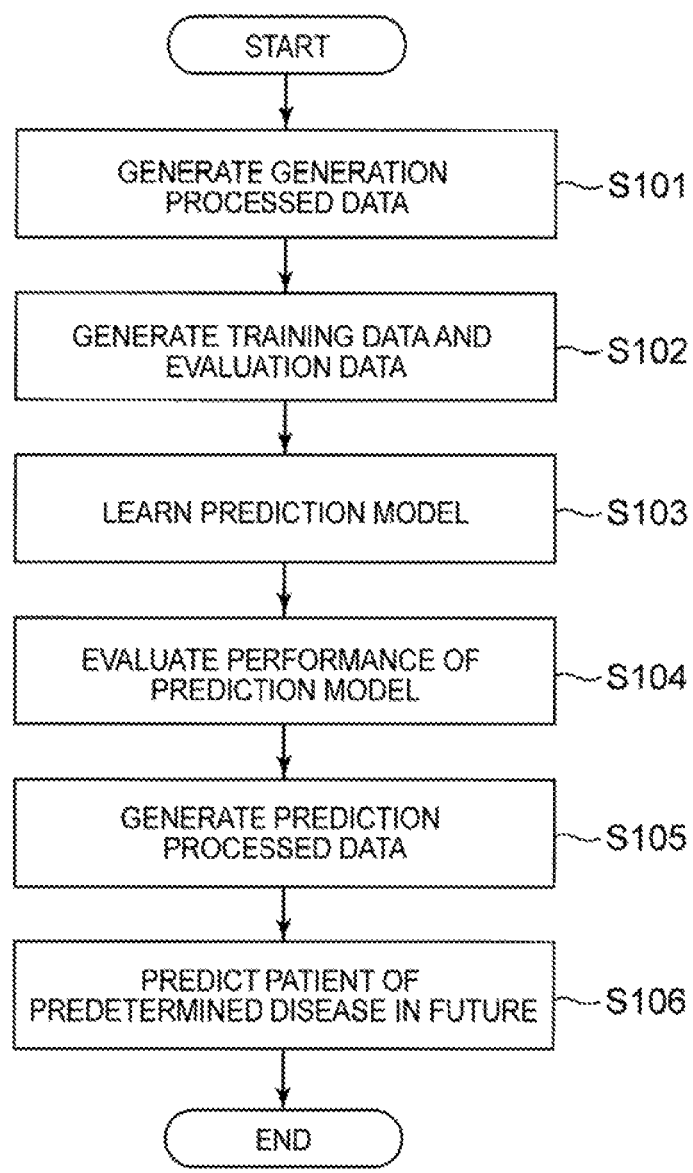
FIG. 12 is a flowchart showing operation of a disease patient prediction process by the disease development risk prediction system 100 according to Exemplary embodiment 1.

Operation of predicting each patient of a predetermined disease by the disease development risk prediction system 100 according to this exemplary embodiment will be described below, with reference to FIG. 12. FIG. 12 is a flowchart showing operation of a disease patient prediction process by the disease development risk prediction system 100 according to Exemplary embodiment 1.

First, the generation data processing means 121 generates processed data for prediction model generation, by aggregating various data input from the storage unit 110 in a personal unit (step S101). The generated processed data is stored in the generation processed data storage means 122.

Next, the data classification means 123 generates training data used for the generation of the prediction model and evaluation data used for the evaluation of the prediction model, on the basis of the processed data stored in the generation processed data storage means 122 (step S102). The generated data is stored in the training data storage means 124 or the evaluation data storage means 125.

Next, the prediction model learning means 131 learns the prediction model using the training data stored in the training data storage means 124 (step S103).

Next, the performance evaluation means 132 evaluates the prediction performance of the learned prediction model using the evaluation data stored in the evaluation data storage means 125 (step S104). For example, only such a prediction model whose evaluated prediction performance satisfies a predetermined criterion is input to the prediction unit 140.

Next, the prediction data processing means 141 generates processed data for prediction, by aggregating various data input from the storage unit 110 in a personal unit (step S105). The generated processed data is stored in the prediction processed data storage means 142.

Next, the prediction means 143 predicts each insured person who has a potential to become a patient of the predetermined disease using the prediction model learned by the prediction model learning means 131, on the basis of the processed data stored in the prediction processed data storage means 142 (step S106). After the prediction, the disease development risk prediction system 100 ends the disease patient prediction process.

Example

Specific examples in which the disease development risk prediction system 100 according to this exemplary embodiment predicts patients of a predetermined disease will be described below, with reference to FIGS. 13 to 19. FIG. 13 is an explanatory diagram showing an example of data aggregated in a personal unit, which is generated by the data classification means 123.

The data shown in FIG. 13 is data after the data classification means 123 performs each process shown in FIGS. 10 to 11 on the processed data stored in the generation processed data storage means 122. That is, processed data of each insured person affected with the predetermined disease before or in a reference year is excluded.

Data of one row in FIG. 13 corresponds to data of one person. That is, the data shown in FIG. 13 is data of ten persons. The age in FIG. 13 is age in year X, and is a continuous value. In the gender in FIG. 13, "0" represents male, and "1" represents female.

In the nursing care level in FIG. 13, "1" represents "needed support level 1", "2" represents "needed support level 2", "3" represents "nursing care level 1", "4" represents "nursing care level 2", "5" represents "nursing care level 3", "6" represents "nursing care level 4", and "7" represents "nursing care level 5". That is, the nursing care level in year X is converted to a continuous value, as mentioned above. For example, the nursing care level is set to a value representing the condition of the insured person at the end of the year.

In the nursing care service use in FIG. 13, "1" represents "used", and "0" represents "not used". For example, in the case where the service use count is more than or equal to threshold m, the nursing care service use is determined as "used".

In disease 1 to disease 5 in FIG. 13, "1" represents "affected before or in year X", and "0" represents "not affected before or in year X". For example, in the case where the number of times the target injury/disease code appears in the medical receipts from year X backward is more than or equal to threshold k, the disease is determined as "affected before or in year X".

In drug efficacy 1 to drug efficacy 5 in FIG. 13, "1" represents "dispensing conducted before or in year X", and "0" represents "no dispensing conducted before or in year X". For example, in the case where the number of times the target national health insurance drug list appears in the dispensing receipts from year X backward is more than or equal to threshold n, "dispensing conducted before or in year X" is determined.

An objective variable is added at the last column, as shown in FIG. 13. In the objective variable, "1" represents "affected in or after year (X+1)", and "0" represents "not affected in or after year (X+1)".

Figure 14:
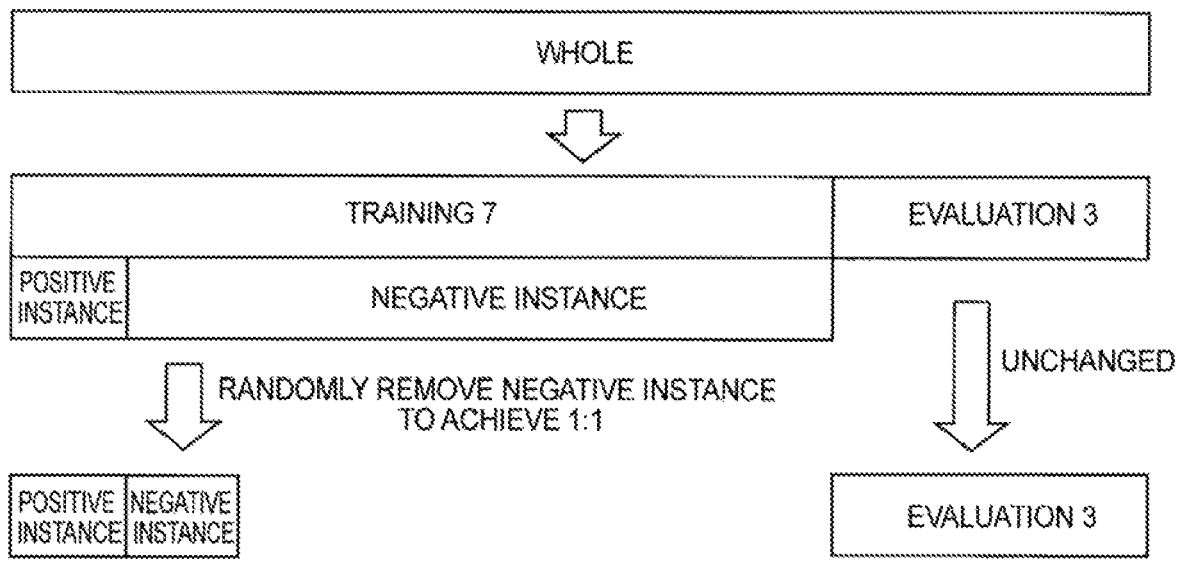
FIG. 14 is an explanatory diagram showing an example of a data classification process by the data classification means 123.

FIG. 14 is an explanatory diagram showing an example of a data classification process by the data classification means 123. After the data shown in FIG. 13 (corresponding to "whole" in FIG. 14) is generated, the data classification means 123 classifies the generated data into training data and evaluation data.

In the example shown in FIG. 14, "training 7" and "evaluation 3" are presented. That is, the data classification means 123 randomly classifies the generated data in a proportion of "training data:evaluation data=7:3". The proportion of the training data and the evaluation data can be designated freely.

FIG. 15 is an explanatory diagram showing an example of the training data and the evaluation data. The upper of in FIG. 15 shows the training data. The under of in FIG. 15 shows the evaluation data.

As shown in FIG. 14, the evaluation data is simply stored in the evaluation data storage means 125 after the classification. The training data is further classified into positive instances whose objective variable is "1" and negative instances whose objective variable is "0".

When the foregoing classification method is used, in the case where the disease subjected to prediction has a low development rate, positive instances are likely to be fewer than negative instances. If positive instances are excessively fewer than negative instances, the prediction model may be unable to be learned appropriately. Accordingly, the data classification means 123 randomly removes negative instances so that "positive instance:negative instance=1:1", as shown in FIG. 14. The proportion of positive instances and negative instances can be designated freely.

FIG. 16 is an explanatory diagram showing an example of a process for the training data by the data classification means 123. The upper of FIG. 16 shows the training data after the classification by the data classification means 123. The data classification means 123 randomly removes negative instances from the training data in the upper of FIG. 16 so that "positive instance:negative instance=1:1".

The under of FIG. 16 shows the training data after the negative instances are randomly removed. The proportion of "0" and "1" in the objective variable of the training data in the under of FIG. 16 is adjusted to "1:1". The adjusted training data in the under of FIG. 16 is stored in the training data storage means 124.

The prediction model learning means 131 learns the prediction model using the training data stored in the training data storage means 124. In this example, the prediction model learning means 131 learns the prediction model based on logistic regression expressed by the following formula.

$$\log_e(p/(1-p))=B_0+B_1X_1+B_2X_2+\ldots+B_pX_p \quad \text{Formula (1)}.$$

In Formula (1), $B_0$ to $B_p$ represent parameters, and $X_1$ to $X_p$ represents explanatory variables. In Formula (1), the value of $\log_e(p/(1-p))$ is logit (logarithmic odds), and is used as a discrimination score. The discrimination score is a score representing the risk of developing the predetermined disease.

Figure 17:
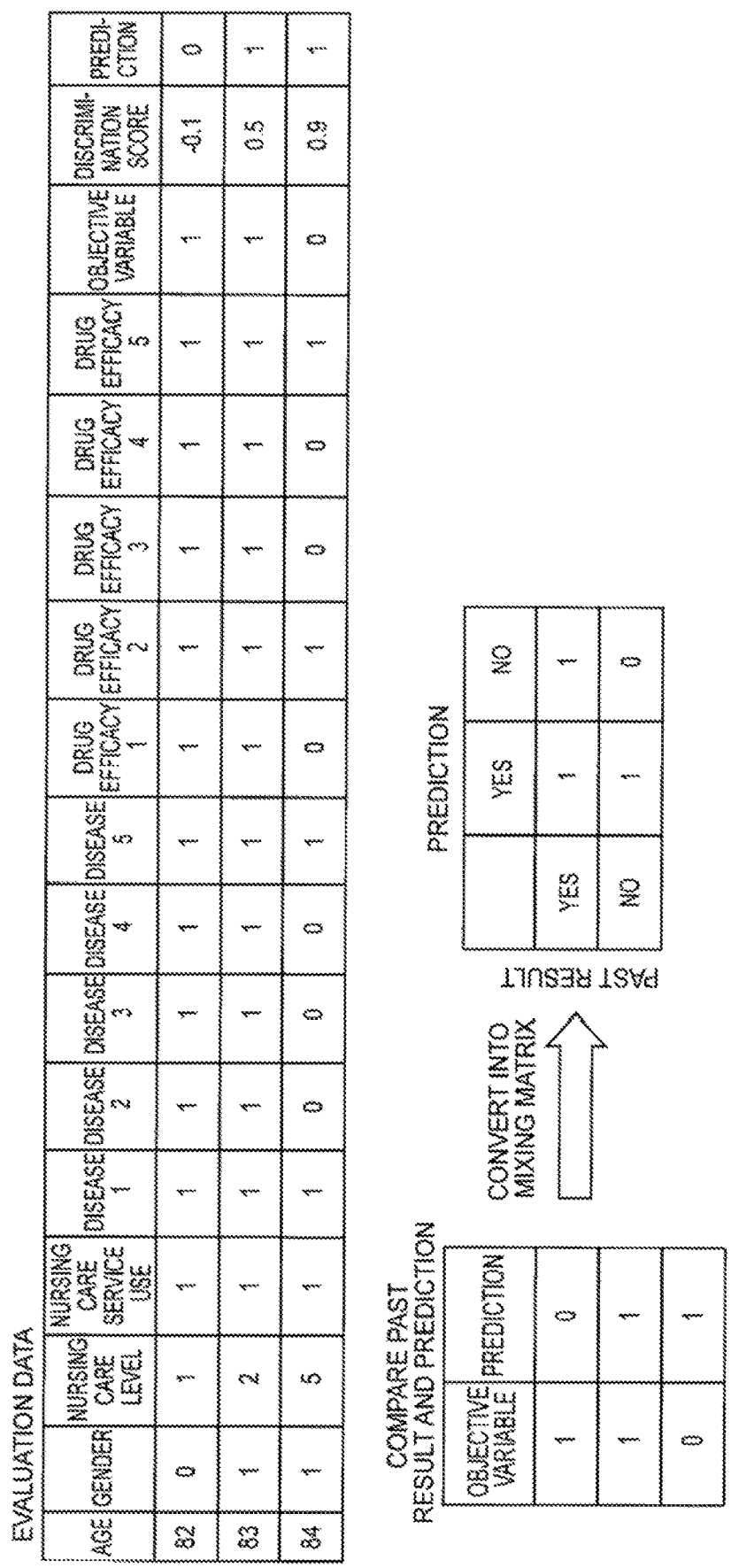
FIG. 17 is an explanatory diagram showing an example of a performance evaluation process by a performance evaluation means 132.

The performance evaluation means 132 evaluates the prediction performance of the generated prediction model using the evaluation data stored in the evaluation data storage means 125. FIG. 17 is an explanatory diagram showing an example of a performance evaluation process by the performance evaluation means 132.

The upper of FIG. 17 shows the evaluation data used by the performance evaluation means 132. As shown in the upper of FIG. 17, the number of evaluation samples in this example is 3. Items of discrimination score and prediction are added at the last columns of the evaluation data.

The discrimination score is a value computed for each set of evaluation data according to the foregoing Formula (1). The prediction stores a value corresponding to the discrimination score. Specifically, the prediction stores "1" in the case where the discrimination score is more than or equal to a given threshold t, and stores "0" in the case where the discrimination score is less than t. The given threshold t is typically set to 0.

The under of FIG. 17 shows a comparison process by the performance evaluation means 132. As shown in the under of FIG. 17, the performance evaluation means 132 compares the objective variable and the prediction of each sample. The performance evaluation means 132 then converts the comparison result into a mixing matrix.

As indicated by the comparison results, there are one sample of "past result: yes, prediction: yes", one sample of "past result: yes, prediction: no", and one sample of "past result: no, prediction: yes". Accordingly, in the mixing matrix in the under of FIG. 17, "1" is stored in each cell other than "past result: no, prediction: no".

FIG. 18 is an explanatory diagram showing an example of values representing performance computed on the basis of the mixing matrix. As shown in FIG. 18, the performance evaluation means 132 can compute values representing performance such as accuracy and precision, using the generated mixing matrix.

The performance evaluation means 132 can also use evaluation indexes such as f value and AUC (Area under the receiver operator curve) as values representing performance. For example, only such a prediction model whose value representing performance is more than or equal to a predetermined value is used in the prediction unit 140.

Figure 19:
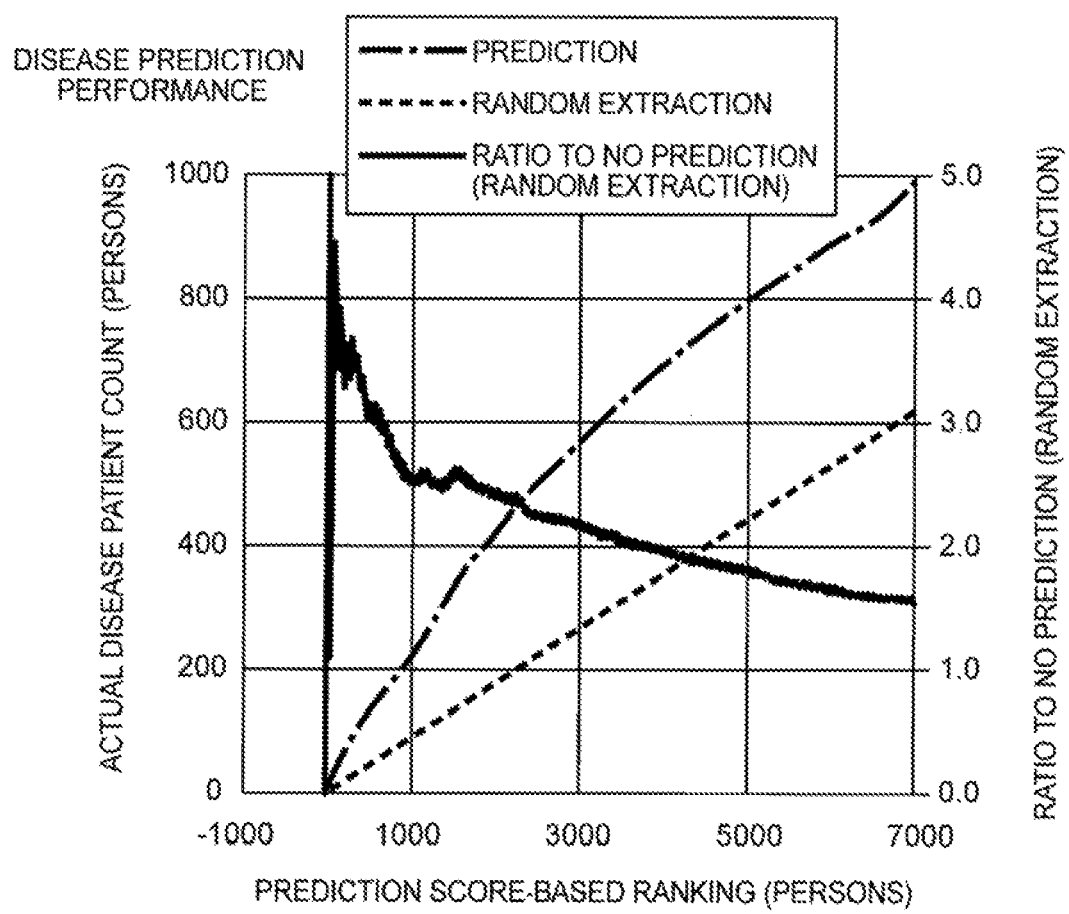
FIG. 19 is an explanatory diagram showing an example of a graph representing disease development prediction performance of a prediction model.

FIG. 19 shows the performance of the prediction model generated by the foregoing process. FIG. 19 is an explanatory diagram showing an example of a graph representing the disease development prediction performance of the prediction model. In the graph in FIG. 19, prediction precision is displayed for insured persons in descending order of prediction score.

In the prediction model of the example shown in FIG. 19, processed data of one year is used for the explanatory variable, and processed data of three years is used for the objective variable. That is, the prediction model of the example predicts the risk of developing the predetermined disease within three years.

Moreover, in the case where the lowest annual use count of nursing care service is more than or equal to threshold m, in the case where the lowest receipt count of disease is more than or equal to threshold k, and in the case where the lowest prescription receipt count of dispensing is more than or equal to threshold n, the nursing care service use, the target disease, and the target drug efficacy as explanatory variables in FIG. 13 are respectively set to "1".

In this example, the data classification means 123 classifies the generated data into training data and evaluation data in a proportion of "7:3". The data classification means 123 also adds negative instances to the training data so that the proportion of positive instances and negative instances is "1:2".

The data classification means 123 also adds negative instances to the evaluation data so that the proportion of positive instances and negative instances is the actual disease development rate. Positive instances and negative instances used for learning or evaluation of the prediction model are randomly selected from each of the training data and the evaluation data.

The horizontal axis of the graph in FIG. 19 represents prediction score-based ranking (persons). In the graph in FIG. 19, insured persons are arranged in descending order of prediction score output from the prediction model. That is, an insured person with a smaller value is predicted as being more likely to develop the predetermined disease in the future.

The left vertical axis of the graph in FIG. 19 represents the actual disease development count (persons). The dashed-dotted line in FIG. 19 represents the number of persons who actually developed the disease from among the insured persons predicted by the prediction model. The broken line in FIG. 19 represents the number of persons who actually developed the disease from among randomly extracted insured persons.

The right vertical axis of the graph in FIG. 19 represents the ratio to "no prediction" (random extraction). The solid line in FIG. 19 represents the ratio of the number of persons represented by the dashed-dotted line in FIG. 19 to the number of persons represented by the broken line in FIG. 19. The graph in FIG. 19 represents the ratio of the extracting power of the prediction model to random sampling.

That is, when the prediction model generated in this example is used, insured persons developing the predetermined disease in the future are predicted with a higher probability than when insured persons are randomly extracted. The scale in the left vertical axis of the graph in FIG. 19 may be accuracy or precision shown in FIG. 18, AUC, or the like.

Description of Effects

When AI-related technology is applied to medical care-related data such as receipts, the data processing unit 120 in this exemplary embodiment can generate records for each individual person on the basis of medical care-related data. The data processing unit 120 can generate records while maintaining the anonymity of each individual person.

That is, the anonymity of each individual person is maintained in the case where the prediction model generation unit 130 in this exemplary embodiment learns the prediction model. With use of the disease development risk prediction system 100 according to this exemplary embodiment, a plurality of sets of data from different sources is utilized for learning data of a disease development risk prediction model while protecting personal information.

The prediction unit 140 in this exemplary embodiment can predict the risk at which an insured person who has agreed use of personal information by a third party develops the predetermined disease. The disease development risk prediction system 100 according to this exemplary embodiment can thus predict each insured person who has a potential to become a patient of the predetermined disease.

The disease development risk prediction system 100 according to this exemplary embodiment may be, for example, realized by a processor that executes a process according to a program stored in a non-transitory storage medium. That is, the generation data processing means 121, the data classification means 123, the prediction model learning means 131, the performance evaluation means 132, the prediction data processing means 141, and the prediction means 143 may be, for example, realized by a processor that executes a process according to program control. The processor is, for example, a central processing unit (CPU) or a graphics processing unit (GPU).

The medical receipt storage means 111, the dispensing receipt storage means 112, the nursing care insurance data storage means 113, the generation processed data storage means 122, the training data storage means 124, the evaluation data storage means 125, and the prediction processed data storage means 142 may be, for example, realized by random access memory (RAM).

Each component in the disease development risk prediction system 100 according to this exemplary embodiment may be realized by a hardware circuit. As an example, the medical receipt storage means 111, the dispensing receipt storage means 112, the nursing care insurance data storage means 113, the generation data processing means 121, the generation processed data storage means 122, the data classification means 123, the training data storage means 124, the evaluation data storage means 125, the prediction model learning means 131, the performance evaluation means 132, the prediction data processing means 141, the prediction processed data storage means 142, and the prediction means 143 are each realized by large scale integration (LSI) such as a field programmable gate array (FPGA). These components may be realized by one FPGA.

Figure 20:
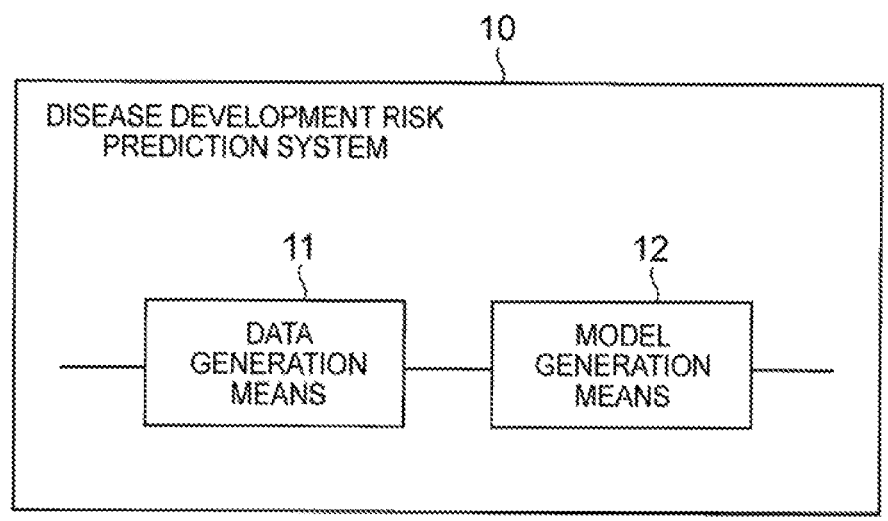
FIG. 20 is a block diagram showing an overview of a disease development risk prediction system according to the present invention.

An overview of the present invention will be described below. FIG. 20 is a block diagram showing an overview of a disease development risk prediction system according to the present invention. A disease development risk prediction system 10 according to the present invention includes: a data generation means 11 (e.g. the generation data processing means 121) which generates combination data by combining at least two different types of receipt data using a combination key, wherein the receipt data includes an insured person number for an insured person which was converted using a predetermined method, a birth date or birth year and month which are both age-identifiable items, and gender, and the combination key combines the converted insured person number, age-identifiable items, and gender; and a model generation means 12 (e.g. the prediction model learning means 131) which uses the generated combination data to generate a prediction model predicting a risk of the insured person of developing a predetermined disease.

With such a structure, the disease development risk prediction system can predict disease development risk on the basis of a plurality of sets of data from different sources while protecting personal information.

The data generation means 11 may combine the at least two different types of receipt data using the combination key including the insured person number anonymized by hashing or encryption.

With such a structure, the disease development risk prediction system can generate the prediction model with higher level of personal information protection.

The receipt data may be any of: medical receipt data that is data indicating a receipt for a medical act; dispensing receipt data that is data indicating a receipt for a dispensing act; and nursing care insurance data that is data indicating a receipt for a nursing care service.

The disease development risk prediction system 10 may include a prediction means (e.g. the prediction means 143) which predicts an insured person having a potential to become a patient of the predetermined disease, using the generated prediction model, wherein the data generation means 11: generates the combination data using at least the medical receipt data; excludes, from the generated combination data, data of an insured person who developed the predetermined disease before or in a predetermined year; and adds, to the combination data from which the data of the insured person who developed the predetermined disease has been excluded, an attribute indicating whether the insured person developed the predetermined disease in or after a year following the predetermined year, and wherein the model generation means 12 generates the prediction model, using the added attribute as an objective variable and using, as an explanatory variable, information from the predetermined year backward included in the combination data from which the data of the insured person who developed the predetermined disease has been excluded.

With such a structure, the disease development risk prediction system can generate the prediction model for predicting the risk of the insured person developing the predetermined disease for the first time.

The data generation means 11 may determine an insured person for which the number of times an injury/disease code corresponding to the predetermined disease is included in the medical receipt data from the predetermined year backward or from the year following the predetermined year onward is more than or equal to a designated number, as the insured person who developed the predetermined disease before or in the predetermined year or in or after the year following the predetermined year.

With such a structure, the disease development risk prediction system can more reliably determine whether the insured person develops a disease that is difficult to diagnose.

The model generation means 12 may use a code of middle classification corresponding to an ICD-10 code included in the medical receipt data, as the explanatory variable. The data generation means 11 may generate the combination data using at least the dispensing receipt data, and the model generation means 12 may use a number representing drug efficacy in a national health insurance drug list included in the dispensing receipt data, as the explanatory variable.

With such a structure, the disease development risk prediction system can generate the prediction model of higher prediction precision.

The data generation means 11 may: generates the combination data using the nursing care insurance data; determine an insured person for which the number of times a predetermined national health insurance drug list is included in the dispensing receipt data from the predetermined year backward is more than or equal to a designated number, as an insured person prescribed with a drug indicated by the predetermined national health insurance drug list before or in the predetermined year; and determine an insured person for which the number of times information corresponding to a predetermined nursing care service is included in the nursing care insurance data from the predetermined year backward is more than or equal to a designated number, as an insured person who used the predetermined nursing care service before or in the predetermined year.

With such a structure, the disease development risk prediction system can more reliably determine whether the drug was prescribed and whether the nursing care service was used.

Although the present invention has been described with reference to the exemplary embodiments and examples, the present invention is not limited to the foregoing exemplary embodiments and examples. Various changes understandable by those skilled in the art can be made to the structures and details of the present invention within the scope of the present invention.

The foregoing exemplary embodiments can be wholly or partly described as, but not limited to, the following supplementary notes.

(Supplementary note 1) A disease development risk prediction system including: a data generation means which generates combination data by combining at least two different types of receipt data using a combination key, wherein the receipt data includes an insured person number for an insured person which was converted using a predetermined method and birth year of the insured person, and the combination key combines the converted insured person number and the birth year; and a model generation means which uses the generated combination data to generate a prediction model predicting a risk of the insured person of developing a predetermined disease.

(Supplementary note 2) The disease development risk prediction system according to supplementary note 1, wherein the receipt data includes birth year and month of the insured person, and wherein the data generation means combines the at least two different types of receipt data using a combination key that is a key combining the converted insured person number and the birth year and month.

(Supplementary note 3) The disease development risk prediction system according to supplementary note 2, wherein the receipt data includes gender of the insured person, and wherein the data generation means combines the at least two different types of receipt data using a combination key that is a key combining the converted insured person number, the birth year and month, and the gender.

(Supplementary note 4) The disease development risk prediction system according to any one of supplementary notes 1 to 3, wherein the data generation means combines the at least two different types of receipt data using a combination key including age of the insured person.

(Supplementary note 5) The disease development risk prediction system according to any one of supplementary notes 1 to 4, wherein the data generation means combines the at least two different types of receipt data using the combination key including the insured person number subjected to hashing.

(Supplementary note 6) The disease development risk prediction system according to any one of supplementary notes 1 to 4, wherein the data generation means combines the at least two different types of receipt data using the combination key including the insured person number subjected to encryption.

(Supplementary note 7) The disease development risk prediction system according to any one of supplementary notes 1 to 6, wherein the receipt data is any of: medical receipt data that is data indicating a receipt for a medical act; dispensing receipt data that is data indicating a receipt for a dispensing act; and nursing care insurance data that is data indicating a receipt for a nursing care service.

(Supplementary note 8) The disease development risk prediction system according to supplementary note 7, wherein the data generation means generates the combination data using at least the medical receipt data and the dispensing receipt data.

(Supplementary note 9) The disease development risk prediction system according to supplementary note 8, wherein the data generation means excludes, from the generated combination data, data of an insured person who developed the predetermined disease before or in a predetermined year, and wherein the model generation means generates the prediction model using the combination data from which the data of the insured person has been excluded.

(Supplementary note 10) The disease development risk prediction system according to supplementary note 9, wherein the data generation means determines an insured person for which the number of times an injury/disease code corresponding to the predetermined disease is included in the medical receipt data from the predetermined year backward is more than or equal to a designated number, as the insured person who developed the predetermined disease before or in the predetermined year.

(Supplementary note 11) The disease development risk prediction system according to supplementary note 9 or 10, wherein the data generation means adds, to the generated combination data, an attribute indicating whether the insured person developed the predetermined disease in or after a year following the predetermined year, and the model generation means generates the prediction model, using the added attribute as an objective variable and information from the predetermined year backward included in the combination data as an explanatory variable.

(Supplementary note 12) The disease development risk prediction system according to supplementary note 11, wherein the model generation means uses a code of middle classification corresponding to an ICD-10 code included in the medical receipt data, as the explanatory variable.

(Supplementary note 13) The disease development risk prediction system according to supplementary note 11 or 12, wherein the model generation means uses a number representing drug efficacy in a national health insurance drug list included in the dispensing receipt data, as the explanatory variable.

(Supplementary note 14) The disease development risk prediction system according to any one of supplementary notes 1 to 13, including a prediction means which predicts an insured person having a potential to become a patient of the predetermined disease, using the generated prediction model.

(Supplementary note 15) A disease development risk prediction method including: generating combination data by combining at least two different types of receipt data using a combination key, wherein the receipt data includes an insured person number for an insured person which was converted using a predetermined method and birth year of the insured person, and the combination key combines the converted insured person number and the birth year; and using the generated combination data to generate a prediction model predicting a risk of the insured person of developing a predetermined disease.

(Supplementary note 16) The disease development risk prediction method according to supplementary note 15, wherein the receipt data includes birth year and month of the insured person, and wherein the at least two different types of receipt data are combined using a combination key that is a key combining the converted insured person number and the birth year and month.

(Supplementary note 17) A disease development risk prediction program for causing a computer to execute: a first generation process of generating combination data by combining at least two different types of receipt data using a combination key, wherein the receipt data includes an insured person number for an insured person which was converted using a predetermined method and birth year of the insured person, and the combination key combines the converted insured person number and the birth year; and a second generation process of using the generated combination data to generate a prediction model predicting a risk of the insured person of developing a predetermined disease.

(Supplementary note 18) The disease development risk prediction program according to supplementary note 17, wherein the receipt data includes birth year and month of the insured person, and wherein the computer is caused, in the first generation process, to combine the at least two different types of receipt data using a combination key that is a key combining the converted insured person number and the birth year and month.

REFERENCE SIGNS LIST 10, 100 Disease development risk prediction system
11 Data generation means
12 Model generation means
110 Storage unit
111 Medical receipt storage means
112 Dispensing receipt storage means
113 Nursing care insurance data storage means
120 Data processing unit
121 Generation data processing means
122 Generation processed data storage means
123 Data classification means
124 Training data storage means
125 Evaluation data storage means
130 Prediction model generation unit
131 Prediction model learning means
132 Performance evaluation means
140 Prediction unit
141 Prediction data processing means
142 Prediction processed data storage means

The invention claimed is:

1. A disease development risk prediction system comprising:
a processor;
a memory storing instructions executable by the processor to:
generate combination data by combining at least two different types of receipt data using a combination key, wherein the receipt data includes an insured person number for an insured person which was converted using a predetermined method and birth year of the insured person, and wherein the combination key combines the converted insured person number and the birth year;
generate a machine learning prediction model predicting a risk of the insured person of developing a predetermined disease using generated combination data; and
apply the machine learning prediction model to the generated combination data for the insured person to predict the risk of the insured person of developing the predetermined disease, wherein
the receipt data is any of: medical receipt data indicating a receipt for a medical act; and dispensing receipt data indicating a receipt for a dispensing act,
the processor generates the combination data using at least the medical receipt data and the dispensing receipt data,
the processor excludes, from the generated combination data, data of the insured person who developed the predetermined disease before or in a predetermined year,
the processor generates the machine learning prediction model for predicting the risk of the insured person developing the predetermined disease for a first time, using the combination data from which the data of the insured person has been excluded,
the processor adds, to the generated combination data, an attribute indicating whether the insured person developed the predetermined disease in or after a year following the predetermined year,
the processor generates the machine learning prediction model, using the added attribute as an objective variable and information from the predetermined year backward included in the combination data as an explanatory variable, and
the processor predicts the risk of the insured person developing the predetermined disease for the first time, using the generated machine learning prediction model.

2. The disease development risk prediction system according to claim 1, wherein the receipt data includes the birth year and month of the insured person, and
wherein the processor combines the at least two different types of receipt data using the combination key, and wherein the combination key combines the converted insured person number and the birth year and the month.

3. The disease development risk prediction system according to claim wherein the receipt data includes nursing care insurance data indicating a receipt for a nursing care service.

4. The disease development risk prediction system according to claim 2, wherein the receipt data includes gender of the insured person, and
wherein the processor combines the at least two different types of receipt data using the combination key, and wherein the combination key combines the converted insured person number, the birth year and the month, and the gender.

5. The disease development risk prediction system according to claim 1, wherein the processor combines the at least two different types of receipt data using the combination key including age of the insured person.

6. The disease development risk prediction system according to claim 1, wherein the processor combines the at least two different types of receipt data using the combination key including the insured person number subjected to hashing.

7. The disease development risk prediction system according to claim 1, wherein the processor combines the at least two different types of receipt data using the combination key including the insured person number subjected to encryption.

8. The disease development risk prediction system according to claim 1, wherein the processor determines the insured person for which a number of times an injury/disease code corresponding to the predetermined disease is included in the medical receipt data from the predetermined year backward is more than or equal to a designated number, as the insured person who developed the predetermined disease before or in the predetermined year.

9. The disease development risk prediction system according to claim 1, wherein the processor uses a code of middle classification corresponding to an ICD-10 code included in the medical receipt data, as the explanatory variable.

10. The disease development risk prediction system according to claim 1, wherein the processor uses a number representing drug efficacy in a national health insurance drug list included in the dispensing receipt data, as the explanatory variable.

11. The disease development risk prediction system according to claim 1, wherein the instructions are executable by the processor to further:
predict the insured person having a potential to become a patient of the predetermined disease, using the generated machine learning prediction model.

12. A disease development risk prediction method comprising:
generating combination data by combining at least two different types of receipt data using a combination key, wherein the receipt data includes an insured person number for an insured person which was converted using a predetermined method and birth year of the insured person, and wherein the combination key combines the converted insured person number and the birth year;
generating a machine learning prediction model predicting a risk of the insured person of developing a predetermined disease using generated combination data;
applying the machine learning prediction model to the generated combination data for the insured person to predict the risk of the insured person of developing the predetermined disease, wherein
the receipt data is any of: medical receipt data indicating a receipt for a medical act; and dispensing receipt data indicating a receipt for a dispensing act, further comprising:
generating the combination data using at least the medical receipt data and the dispensing receipt data;
excluding, from the generated combination data, data of the insured person who developed the predetermined disease before or in a predetermined year;
generating the machine learning prediction model for predicting the risk of the insured person developing the predetermined disease for a first time, using the combination data from which the data of the insured person has been excluded;
adding, to the generated combination data, an attribute indicating whether the insured person developed the predetermined disease in or after a year following the predetermined year;
generating the machine learning prediction model, using the added attribute as an objective variable and information from the predetermined year backward included in the combination data as an explanatory variable; and
predicting the risk of the insured person developing the predetermined disease for the first time, using the generated machine learning prediction model.

13. The disease development risk prediction method according to claim 12, wherein the receipt data includes the birth year and month of the insured person, and
wherein the at least two different types of receipt data are combined using the combination key, and wherein the combination key combines the converted insured person number and the birth year and the month.

14. A non-transitory computer-readable capturing medium having captured therein a disease development risk prediction program for causing a computer to execute:
a first generation process of generating combination data by combining at least two different types of receipt data using a combination key, wherein the receipt data includes an insured person number for an insured person which was converted using a predetermined method and birth year of the insured person, and wherein the combination key combines the converted insured person number and the birth year;
a second generation process of generating a machine learning prediction model predicting a risk of the insured person of developing a predetermined disease using generated combination data;
an application process of applying the machine learning prediction model to the generated combination data for the insured person to predict the risk of the insured person of developing the predetermined disease, wherein
the receipt data is any of: medical receipt data indicating a receipt for a medical act; and dispensing receipt data indicating a receipt for a dispensing act,
the computer is caused, in the first generation process, to generate the combination data using at least the medical receipt data and the dispensing receipt data, exclude, from the generated combination data, data of the insured person who developed the predetermined disease before or in a predetermined year, and add, to the generated combination data, an attribute indicating whether the insured person developed the predetermined disease in or after a year following the predetermined year,
the computer is caused, in the second generation process, to generate the machine learning prediction model for predicting the risk of the insured person developing the predetermined disease for a first time, using the combination data from which the data of the insured person has been excluded, the added attribute as an objective variable and information from the predetermined year backward included in the combination data as an explanatory variable, and the computer is caused, in the application process, to predict the risk of the insured person developing the predetermined disease for the first time, using the generated machine learning prediction model.

15. The disease development risk prediction program according to claim 14, wherein the receipt data includes the birth year and month of the insured person, and wherein the computer is caused, in the first generation process, to combine the at least two different types of receipt data using the combination key, wherein the combination key combines the converted insured person number and the birth year and the month.

* * * * *